US006951941B2

(12) United States Patent
Kwiatkowski

(10) Patent No.: US 6,951,941 B2
(45) Date of Patent: Oct. 4, 2005

(54) BI-PLANAR MICROWAVE SWITCHES AND SWITCH MATRICES

(75) Inventor: Regina Kwiatkowski, Cambridge (CA)

(73) Assignee: Com Dev Ltd., Cambridge (CA)

( * ) Notice: Subject to any disclaimer, the term of this patent is extended or adjusted under 35 U.S.C. 154(b) by 177 days.

(21) Appl. No.: 10/359,158

(22) Filed: Feb. 6, 2003

(65) Prior Publication Data

US 2004/0155725 A1 Aug. 12, 2004

(51) Int. Cl.[7] .............................................. C07D 221/20
(52) U.S. Cl. .......................................... 546/16; 546/278
(58) Field of Search ...................... 385/15-19; 333/105, 333/101, 161, 205, 262

(56) References Cited

U.S. PATENT DOCUMENTS 3,358,269 A 12/1967 Benes
3,593,295 A 7/1971 Joel, Jr.
3,993,874 A 11/1976 Arnold et al.

(Continued)

FOREIGN PATENT DOCUMENTS

WO WO 01/13457 A 2/2001

OTHER PUBLICATIONS

Benes, V.E., Mathematical Theory of Connecting Networks and Telephone Traffic, New York: Academic Press, 1965, pp. 82–87, 96–97, 120–125.

Clos, Charles, "A Study of Non–Blocking Switching Networks", The Bell System Technical Journal, vol. XXXII, Mar. 1953, pp. 406–424.

Glenn, T.P., S. Webster, Packaging the Micro–machine, Amkor Technology, pp. 1–6.

Kathei, Linda P.B., Micro–Machined RF Front Ends for High Frequency Communication Systems, presentation from MTT Conference, 1999.

Kautz, William, H., Karl N. Levitt and Abraham Waksman, "Cellular Interconnection Arrays", IEEE Trans. on Computers, vol. C–17, No. 5, May 1968, pp. 443–451.

Kyles, Ian, Creating Large Switch Fabrics using the Three–Stage (Clos) Architecture, Vitesse Semiconductor Corporation, Camarillo, CA, pp. 1–12.

Rebeiz, G., RF MEMS: A New Technology for High–Performance Systems: Series and Shunt Switches–Topology, Fabrication, Measurements, Reliability and Packaging, University of Michigan, EECS Department Radiation Laboratory.

Waksman, Abraham "A Permutation Network", Journal ACM, vol. 15, Jan. 1968, pp. 159–164.

*Primary Examiner*—Rita Desai
(74) *Attorney, Agent, or Firm*—Bereskin & Parr

(57) ABSTRACT

A microwave switch for transmitting signals having a plurality of ports and a plurality of signal paths for selective transmission of the signals. Each signal path is disposed between a respective pair of the ports and each signal path has a conducting state in which signal transmission occurs between the respective pair of ports and a non-conducting state in which signal transmission does not occur between the respective pair of ports. The switch also has a plurality of actuators, each actuator being adapted to actuate at least one of the signal paths between the conducting and non-conducting states. At least one of the ports and at least one of the signal paths are located on a first plane and the remainder of the ports and the signal paths are located on a second plane such that there are no cross over points between the signal paths in any of the planes. A switch matrix can be built using this bi-planar switch such that the switches in the matrix are connected without any cross over points.

17 Claims, 13 Drawing Sheets

U.S. PATENT DOCUMENTS

| | | | | | |
|---|---|---|---|---|---|
| 4,038,638 | A | | 7/1977 | Hwang | |
| 4,245,214 | A | | 1/1981 | Beirne | |
| 4,254,385 | A | | 3/1981 | Childs et al. | |
| 4,317,972 | A | | 3/1982 | Kjellberg | |
| 4,330,766 | A | | 5/1982 | Pentlicki | |
| 4,566,007 | A | | 1/1986 | Richards | |
| 4,654,842 | A | | 3/1987 | Coraluppi et al. | |
| 4,789,762 | A | | 12/1988 | Miller et al. | |
| 4,851,801 | A | | 7/1989 | Engel | |
| 4,908,588 | A | | 3/1990 | Hoffman et al. | 333/105 |
| 4,924,196 | A | | 5/1990 | Uyeda | |
| 4,931,802 | A | | 6/1990 | Assal et al. | |
| 4,988,993 | A | | 1/1991 | Hwang et al. | |
| 5,220,320 | A | | 6/1993 | Assal et al. | |
| 5,401,912 | A | | 3/1995 | Mattei | |
| 5,451,918 | A | | 9/1995 | Sun | |
| 5,469,001 | A | | 11/1995 | Vaillant | |
| 5,578,976 | A | | 11/1996 | Yao | |
| 5,652,558 | A | | 7/1997 | Leikus et al. | |
| 5,754,118 | A | | 5/1998 | Brunner | |
| 5,757,252 | A | | 5/1998 | Cho et al. | |
| 5,828,268 | A | | 10/1998 | Ando et al. | |
| 5,883,556 | A | | 3/1999 | Shutes | |
| 5,932,936 | A | | 8/1999 | Potthast et al. | |
| 5,936,482 | A | | 8/1999 | Ando et al. | |
| 6,016,092 | A | | 1/2000 | Qiu et al. | |
| 6,018,523 | A | | 1/2000 | Even | |
| 6,037,849 | A | | 3/2000 | Ciezarek | |
| 6,064,126 | A | | 5/2000 | Beardmore | |
| 6,064,127 | A | | 5/2000 | Vaillant | |
| 6,100,477 | A | | 8/2000 | Randall et al. | |
| 6,133,807 | A | | 10/2000 | Akiyama et al. | |
| 6,229,683 | B1 | | 5/2001 | Goodwin-Johansson | |
| 6,252,473 | B1 | | 6/2001 | Ando | |
| 6,291,908 | B1 | | 9/2001 | Tran et al. | |
| 6,307,169 | B1 | | 10/2001 | Sun et al. | |
| 6,320,145 | B1 | | 11/2001 | Tai et al. | |
| 6,346,744 | B1 | | 2/2002 | Geller | |
| 6,366,716 | B1 | * | 4/2002 | Graves | 385/17 |
| 6,658,177 | B1 | * | 12/2003 | Chertkow | 385/18 |
| 6,690,847 | B2 | * | 2/2004 | Hsu | 385/16 |
| 6,849,924 | B2 | * | 2/2005 | Allison et al. | 257/635 |
| 2001/0006361 | A1 | | 7/2001 | Cayrou et al. | |
| 2001/0048141 | A1 | | 12/2001 | Lin et al. | |
| 2002/0009255 | A1 | | 1/2002 | Lebouett'e et al. | |
| 2002/0020905 | A1 | | 2/2002 | McCormack et al. | |
| 2002/0027064 | A1 | | 3/2002 | York et al. | |

* cited by examiner

BI-PLANAR MICROWAVE SWITCHES AND SWITCH MATRICES

FIELD OF THE INVENTION

The present invention relates to microwave switches. In particular, the present invention relates to bi-planar electro-mechanical and MEMS microwave switches and Switch Matrices.

BACKGROUND OF THE INVENTION

Microwave switches are often used in satellite communication systems where reliability of system components is important. Accordingly, microwave switches are commonly used in Switch Routing Matrices or in Redundancy Rings. The Switch Routing Matrices allow for a number of inputs to be connected to a number of outputs of the matrix. There are two groups of Switch Routing Matrices: one group being the non-blocking and non-interrupting such as crossbar or crosspoint switch matrices; the other group being just non-blocking switch routing matrices, such as rearrangeable switch matrices, diamond switch matrices, rectangular switch matrices, rhomboidal switch matrices, pruned rectangular switch matrices, Bose-Nelson switch matrices, etc. The Redundancy Rings are switch arrays that have usually one or two columns of T-switches (for input) and reroute a number of channels to spare Traveling Wave Tube Amplifiers (TWTA) in case of TWTA failure. The preference there is to use the T-switches to create the redundancy rings with the minimum number switches that are capable to match the output redundancy rings.

In the current switch matrix architectures there are always cross over points between signal paths either between switches or internal to a microwave switch since the signal paths are on the same plane in both cases. The cross over points of signal paths result in design and performance problems both for coaxial and planar technology.

In general, the RF electromechanical switches currently used to implement RF switch matrices are usually bulky and increase the mass of the switch matrix. Furthermore, the use of cables to achieve all required connections results in increased mass and volume of the assembly and increase RF losses for the matrix. This can be significant since switch matrices are used in spacecraft applications where low mass is important.

However, there is currently a movement towards the development of RF MEMS (Micro Electro-Mechanical Systems) switches. These are a new class of planar devices distinguished by their extremely small dimensions and the fabrication technology, which is similar to integrated circuits and allows for batch machining. An RF MEMS switch is constructed on a substrate of an integrated circuit and has a micro-structure with an active element that moves in response to a control voltage, or other control techniques as is commonly known to those skilled in the art, to provide the switching function.

RF MEMS switches have a number of advantages over RF electro-mechanical switches. For instance, since RF MEMS switches are batch machined, their cost represents only a small fraction of the cost of an equivalent conventional bulky electro-mechanical RF switch. Also, the cost does not increase significantly with the number of switches manufactured. Furthermore, since a typical spacecraft employs several hundred microwave switches, the light weight of an RF MEMS switch will provide a reduction in weight which can result in significant cost savings.

However, currently there are no commercially available RF MEMS switch matrices.

SUMMARY OF THE INVENTION

The present invention is directed towards a bi-planar configuration for RF switch matrices and redundancy ring networks using microwave switches such as C-switches and T-switches. The bi-planar configuration is applicable to both RF electro-mechanical switches and RF MEMS switches and involves constructing a switch configuration with no crossing points on a first plane and a corresponding switch configuration with no crossing points on a second plane. The final configuration of the matrix is obtained by connecting the two planar configurations. This bi-planar configuration is particularly suited for Switch Routing Matrices but it can also be applied for Redundancy Rings. The bi-planar structure may also be applied to R switches, S switches and SPDT switches.

In a first aspect, the present invention provides a microwave switch for transmitting signals. The switch comprises a plurality of ports, a plurality of signal paths for selective transmission of the signals, each signal path being disposed between a respective pair of said ports and each signal path having a conducting state in which signal transmission occurs between the respective pair of ports and a non-conducting state in which signal transmission does not occur between the respective pair of ports; and, a plurality of actuators, each actuator being adapted to actuate at least one of the signal paths between the conducting and non-conducting states. At least one of the ports and at least one of the signal paths are located on a first plane and another of the ports and another of the signal paths are located on a second plane whereby, in any of the planes, there are no cross over points between the signal paths.

In a second aspect, the present invention provides a microwave switch network comprising a plurality of input ports, a plurality of output ports, and a plurality of switches connected to one another according to a network configuration with at least one of the switches being connected to the input ports and at least one of the switches being connected to the output ports. The microwave switch network comprises two planes and at least some of said switches are bi-planar switches each having portions constructed on both of the planes for allowing the bi-planar switches to be connected to one another with no cross over points on any of the planes.

BRIEF DESCRIPTION OF THE DRAWINGS

For a better understanding of the present invention and to show more clearly how it may be carried into effect, reference will now be made, by way of example only, to the accompanying drawings which show preferred embodiments of the invention and in which.

DETAILED DESCRIPTION OF THE INVENTION

Figure 1A:
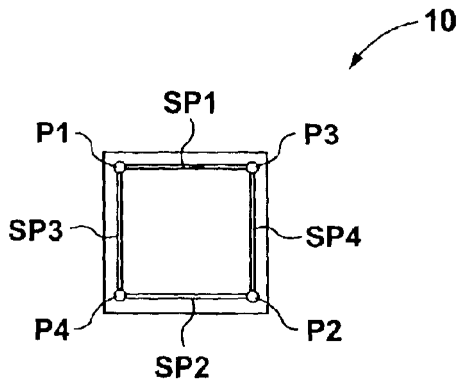
FIG. 1a (Prior Art)
FIG. 1*a* is a top view of a schematic of a prior art C-switch.

Referring now to FIG. 1*a,* shown therein is a schematic for a prior art C-switch 10 which may be implemented as an RF electromechanical switch or an RF MEMS switch as is known to those skilled in the art. The C-switch 10 comprises two input ports P1 and P2, two output ports P3 and P4 and four signal paths SP1, SP2, SP3 and SP4. The signal paths can be considered to be transmission lines. Signal path SP1 connects input port P1 to output port P3, signal path SP2 connects input port P2 to output port P4, signal path SP3 connects input port P1 to output port P4 and signal path SP4 connects input port P2 to output port P3. The position of the input port P2 and the output port P4 have been reversed, as is commonly known to those skilled in the art, to allow a physical realization of a C switch in which the signal paths are on one plane and do not overlap within the switch itself. The configuration shown in FIG. 1*a* is the most widely employed configuration for a C-switch.

The signal paths SP1, SP2, SP3 and SP4 are either closed or open. When a signal path is closed or in a conducting state, an input port is connected to an output port, and when a signal path is open or in a non-conducting state, an input port is not connected to an output port. In use, the C-switch 10 has two positions. In a first position, input port P1 is connected to output port P3 and input port P2 is connected to output port P4 (i.e. signal paths SP1 and SP2 are closed while signal paths SP3 and SP4 are open). In a second position, input port P1 is connected to output port P4 and input port P2 is connected to output port P3 (i.e. signal paths SP3 and SP4 are closed while signal paths SP1 and SP2 are open). The signal paths SP1, SP2, SP3 and SP4 may each be implemented using separate single-pole single-throw (SPST) switches. Alternatively, since only one of signal paths SP1 and SP3 are closed at the same time and since only one of signal paths SP2 and SP4 are closed at the same time, a single-pole double-throw (SPDT) switch may be used to implement signal paths SP1 and SP3 and another SPDT switch may be used to implement signal paths SP2 and SP4.

Figure 1B:
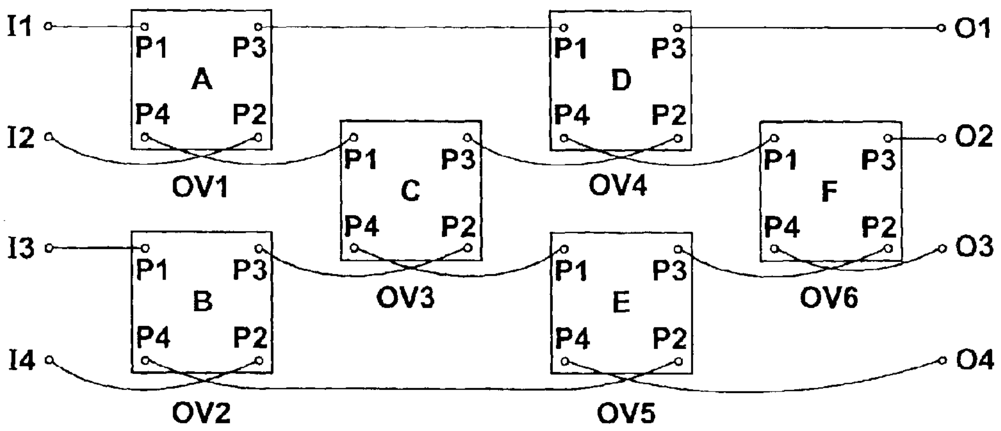
FIG. 1b (Prior Art)
FIG. 1*b* is a top view of a schematic of a prior art switch matrix employing a plurality of switches in accordance with the prior art C-switch of FIG. 1*a;*

Referring now to FIG. 1*b,* shown therein is a schematic of a 4×4 (i.e. 4 inputs and 4 outputs) switch matrix 20 that comprises four inputs I1, I2, I3 and I4, four outputs O1, O2, O3 and O4 and a plurality of C-switches in accordance with C-switch 10 arranged as shown and identified as A, B, C, D, E and F. The switch matrix 20 is configured in a diamond configuration and can permute any of the 4 inputs I1, . . . , I4 onto any of the 4 outputs O1, . . . , O4 in an arbitrary fashion. Various other matrices of C-switches 10 can be built and the switch matrix 20 is shown as an example only. The various other switch matrices will differ from one another in terms of shape, the total number of C-switches required, the number and length of peripheral connectors and the length of the inter-switch connections as is well known to those skilled in the art.

In the switch matrix 20, it can be seen that a number of overlapping connections OV1, OV2, OV3, OV4, OV5 and OV6 are required in connecting the C-switches to each other. This is because the inputs of a trailing C-switch such as C switch B must be connected to the outputs of a leading C-switch such as C switch A. As mentioned previously, the overlapping connections are disadvantageous since this results in design and performance problems.

Figure 2A:
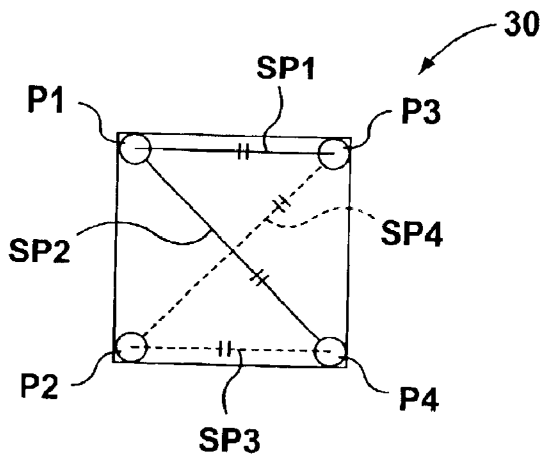
FIG. 2*a* is a top view of a schematic of a bi-planar C-switch in accordance with the present invention.
Figure 2B:
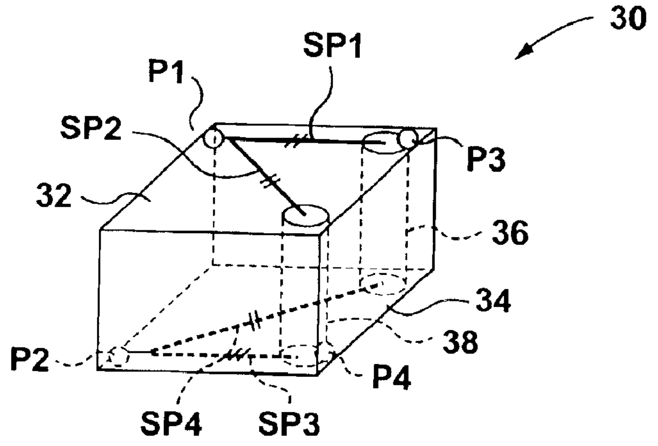
FIG. 2*b* is an isometric view of the schematic of the bi-planar C-switch of FIG. 2*a;*

Referring now to FIGS. 2*a*–2*b,* shown therein is a schematic of a bi-planar C-switch 30 in accordance with the present invention. FIG. 2*a* depicts a top-view of the bi-planar C-switch 30 and FIG. 2*b* depicts an isometric view of the bi-planar C-switch 30. As shown in FIG. 2*a,* the bi-planar C-switch 30 has both input ports P1 and P2 on a first side of the switch 30 and both output ports P3 and P4 on a second side of the switch 30. However, as is more easily seen in FIG. 2*b,* the bi-planar C-switch 30 now has an upper plane 32 in which the ports P1 and P3 and the signal paths SP1 and SP2 are located and a lower plane 34 in which the ports P2 and P4 and the signal paths SP3 and SP4 are located. The bi-planar C-switch 30 also has signal vias 36 and 38 which can be used to connect a signal path located on one of the planes 32 and 34 to an output port located on one of the other of the planes 32 and 34. The input and output ports can be connected to an external interface using conventional methods known to those skilled in the art. Each signal path is operable between a conducting state and a non-conducting state as explained previously. Furthermore, the signal paths may be also implemented using SPST switches. In addition, if desired, a grounding plane (not shown) may be interposed between the planes 36 and 38 to improve the electrical performance by avoiding cross-talk between the signal paths on the different planes.

Figure 2C:
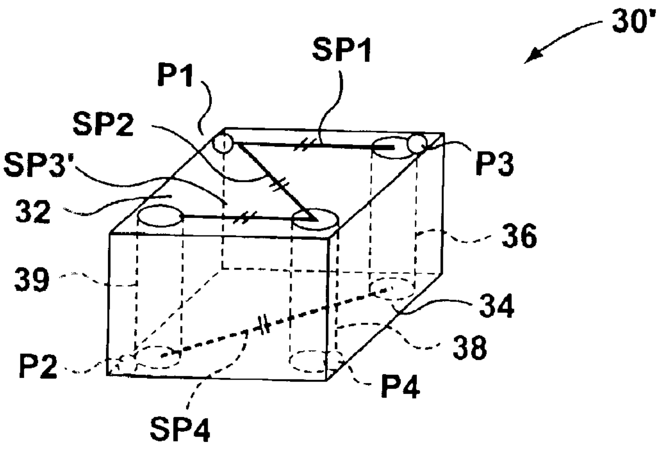
FIG. 2*c* is a isometric view of the schematic of an alternate embodiment of the bi-planar C-switch.

In another alternative embodiment, one of the signal paths may be on one plane with the remaining signal paths located on a different plane. For instance, referring to FIG. 2*c,* shown therein is an alternate embodiment of a bi-planar C-switch 30'. An extra via 39 has been inserted so that signal path SP3' may be moved to plane 34 and still remain in contact with port P2. In this case, signal paths SP3' and SP4 can be implemented by SPST switches.

In alternative embodiments, the locations of the ports may be rearranged so that port P3 is located on the lower plane 34 and the port P4 is located on the upper plane 32. Alternatively, ports P1, P3 and P4 may be on the same plane. However, the ports are preferably located as shown to provide non-overlapping connections when the bi-planar C-switch 30 is used to construct a switch matrix (as discussed further below). Furthermore, the signal paths SP1, SP2, SP3 and SP4 may be implemented by SPDT switches rather than SPST switches.

The bi-planar C-switch 30 may be implemented using an RF MEMS switch or using an RF electromechanical switch as will be discussed further below. If the bi-planar C-switch 30 were embodied in an RF electromechanical switch, the switch would have two RF cavities, each corresponding to one of the planes 32 and 34, within which transmission lines representing each signal path SP1, SP2, SP3 and SP4 would be located. One of the RF cavities could be placed in the upper portion of an RF module and the other of the RF cavities could be placed in the lower portion of another RF module. In this case the waveguide walls form a grounding plane that separates the upper and lower portions of the RF modules preventing cross talk between the signal paths on one plane and the signal paths on another plane. Each waveguide transmission line would comprise a channel containing a moveable reed, which could be connected to the appropriate ports when the reeds are actuated. The connections would either be a direct connection to a port or a connection to the port through a via (this is explained and shown further below). A signal path would be closed by actuating the corresponding reed to come into contact with the two corresponding ports at either end of the signal path. In contrast, a signal path would be opened by actuating the corresponding reed to be grounded.

If the bi-planar C-switch 30 was implemented using an RF MEMS switch, then the planes 32 and 34 could be the opposite surfaces of an IC substrate or the surfaces of two IC substrates. In each case, the substrate surfaces would be connected to each other preferably by using vias (as explained further below). Furthermore, any SPST or SPDT RF MEMS switch known to those skilled in the art could be used to construct the bi-planar C-switch 30. This is discussed in more detail below.

Figure 3A:
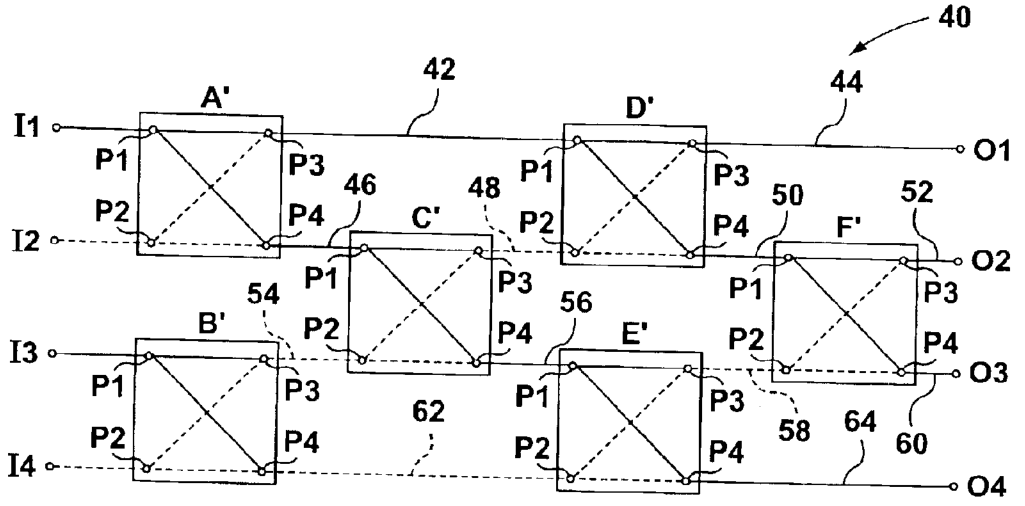
FIG. 3*a* is a top view of a schematic of a bi-planar switch matrix employing a plurality of switches which are each in accordance with the bi-planar C-switch of FIG. 2*a;*

By placing the signal paths on different planes of the bi-planar C-switch 30, a switch matrix can now be constructed in which there is no crossing over of connections between the switches in one plane regardless of the number of bi-planar C-switches in accordance with C-switch 30 used in the matrix. Referring now to FIG. 3*a,* shown therein is a 4×4 bi-planar switch matrix 40 which uses a plurality of bi-planar C-switches 30 identified as A', B', C', D', E' and F' which correspond to the C-switches A, B, C, D, E and F shown in switch matrix 20. The connections between the various C-switches in the switch matrix 40 are no longer overlapping since connections occur on two planes in the switches. Connections and signal paths occurring on the upper plane of the bi-planar switch matrix 40 are shown with solid lines while connections and signal paths shown with dotted lines occur on the bottom plane of the bi-planar switch matrix 40. In particular, connections 42, 44, 46, 50, 52, 56, 60 and 64 occur on a first plane or surface while connections 48, 54, 58 and 62 occur on a second plane or surface. Furthermore, inputs 12 and I4 are connected to ports P2 of C-switches A' and B' on the second plane while outputs O1, O2, O3 and O4 are connected to the appropriate outputs of C-switches D', E' and F' on the first plane. Alternatively, any of the outputs O1, O2, O3 and O4 that are connected to port P3 or port P4 of the bi-planar C-switches D', E' and F' could be placed on either plane due to the signal vias that exist at these ports (i.e. see signal vias 36 and 38 in FIG. 2*b*). However, having the connections 44, 52, 60 and 64 on the same plane may be preferable for installation purposes.

Figure 3B:
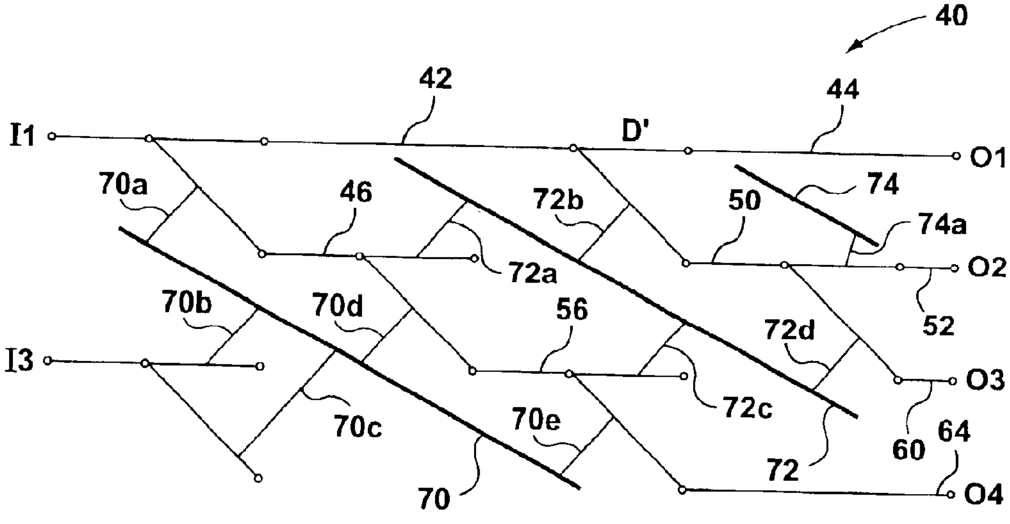
FIG. 3*b* is a top view of the upper plane of the bi-planar switch matrix of FIG. 3*a* showing the position of DC tracks which actuate the upper level of the bi-planar C-switches.

If the bi-planar switch matrix 40 were implemented using RF MEMS switches, then DC tracks 70, 72 and 74 could be laid out as shown in FIG. 3*b,* which shows only the upper surface of the bi-planar switch matrix 40. Each of the DC tracks 70, 72 and 74 provides control lines 70*a* . . . 70*e,* 72*a* . . . 72*d* and 74*a* to actuate the MEMS switch structures to provide open or closed signal paths. As it can be seen, the use of bi-planar RF MEMS switches results in an elegant layout for allowing access from the control lines 70*a* . . . 70*e,* 72*a* . . . 72*d* and 74*a* to the RF MEMS SPST switches.

The DC tracks 70, 72 and 74 may deteriorate the RF behaviour of the bi-planar switch matrix 40 due to coupling between the signal paths and the DC tracks 70, 72 and 74. To avoid this coupling, the DC tracks 70, 72 and 74 are commonly built with a material that has a high resistivity. It is also desirable to have the DC tracks 70, 72 and 74 and the signal paths spaced as far apart from one another which is achieved by laying out the DC tracks 70, 72 and 74 as far as possible from the signal paths with no crossing points as shown in FIG. 3*b*.

The switching structures of the RF MEMS switches in the bi-planar switch matrix 40 comprise electrostatic actuators that move contacts for implementing the switching function (not shown). The actuators require very little current (on the order of nano-Amperes), and therefore high resistively material can be used for DC tracks. This reduces the amount of coupling between the DC tracks 70, 72 and 74 and the signal paths.

Furthermore, implementing a switch matrix using RF MEMS switches allows multiple switches to share the same package which greatly reduces mass and cost since each RF MEMS switch has a very low mass. Also the integration of a switch matrix into an integrated circuit (IC) eliminates the need for cables and other interconnections that represent the bulk of the losses in a switch matrix when the switch matrix is implemented using RF electromechanical switches.

Figure 4A:
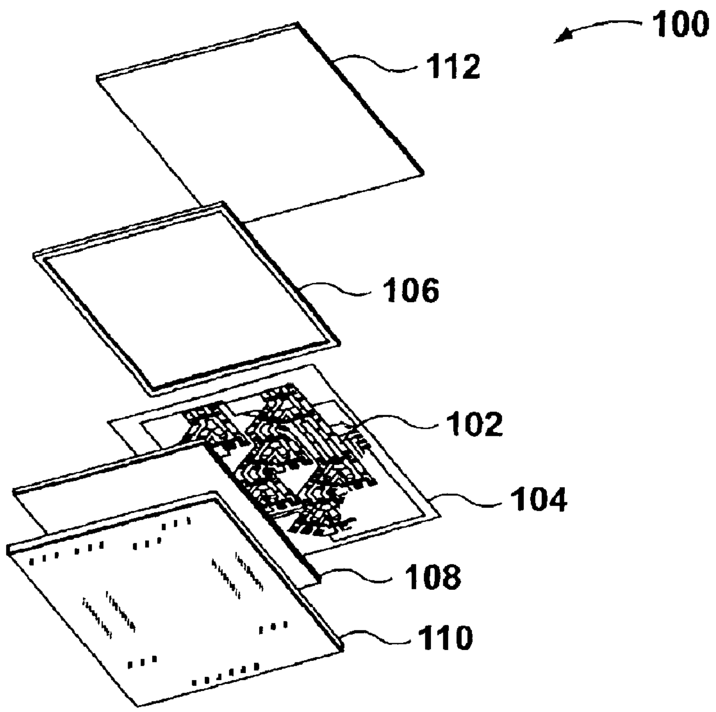
FIG. 4*a* is an exploded view of a switch matrix chip package.

Referring now to FIG. 4*a,* shown therein is an exploded view of an embodiment of a 4×4 Co-Planar Waveguide (CPW) switch matrix chip package 100 that uses RF MEMS switches to implement a bi-planar switch matrix 102. The switch matrix chip 100 comprises a substrate 104 upon which RF MEMS switches are constructed on the upper and lower plane or surfaces thereof. The substrate 104 is sandwiched between an upper protection wafer 106 and a lower protection wafer 108 which both serve to mechanically protect the substrate 104. The lower wafer 108 also has a number of vias (not shown) for allowing connections to be made to the substrate 104. These connections are used to provide input signals and DC bias signals to the bi-planar switch matrix 102 as well as receive output signals there from. These signals are provided by/to an interface layer 110 which has a plurality of pins shown on the bottom surface thereof. The pins may be glass feedthroughs, for interfacing the switch matrix 102 with an RF circuit (not shown) that is external to the chip package 100.

As is commonly known by those skilled in the art, each via is filled with a metal having a high electrical conductivity to reduce insertion loss and DC losses and a high thermal conductivity to provide a thermal path to cool the chip package 100. The dimensions of the vias will be adapted to reduce signal losses. Each signal via may also be surrounded by a U-shaped via for shielding the signal vias and improving the RF isolation between adjacent signal vias. The design of these vias is well known to those skilled in the art and can be based upon the approaches used in U.S. Pat. Nos. 5,401,912 or 5,757,252.

The switch matrix chip package 100 also comprises a cap 112 with an inner cavity (not shown) that houses the protection wafers 106 and 108 and the substrate 104. The cap 112 may be bonded to the interface layer 110 or connected by another suitable means. The cap 112 may be made from a suitable material to provide structural rigidity to the chip package 100. The packaging provides hermetic sealing to ensure an air tight seal to prevent the ingress of moisture and particulates which may contaminate the switch matrix by impairing the movement of free standing portions of the MEMS switches. The cap 112 also ensures the absence of unwanted resonances and electromagnetic interference from coupling to the switch matrix 102 contained therein.

Figure 4B:
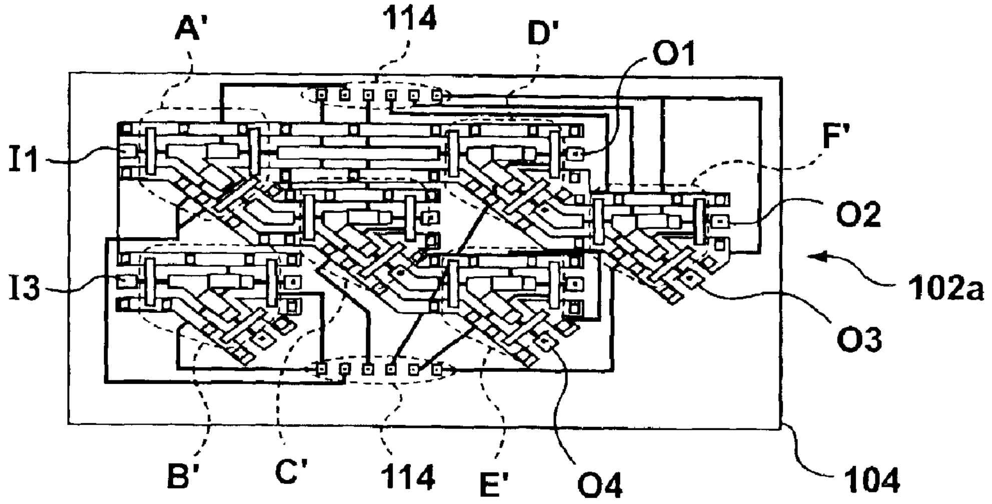
FIG. 4*b* is a top view of a substrate having a bi-planar switch matrix.

Referring now to FIG. 4*b*, shown therein is a top view of the substrate 104 showing the upper portion 102*a* of the bi-planar switch matrix 102 (hereafter referred to as switch matrix 102*a*). The switch matrix 102*a* comprises the upper half of bi-planar C-switches labeled A', B', C', D', E' and F' which correspond to the bi-planar C-switches shown in the bi-planar switch matrix 40. Each upper half of the bi-planar C-switches A', B', C', D', E' and F' comprise an SPDT RF MEMS switch, three shunt air-bridges, an input pad, two output pads and ground lines. These elements are not labeled here to avoid confusion but are labeled in FIG. 4*c* where the upper half of one of the bi-planar C-switches is discussed in more detail. Although SPDT MEMS switches are shown, each SPDT MEMS switch may be replaced by two SPST MEMS switches. Furthermore, larger matrices may be achieved by using the bi-planar switch matrix 102 and appropriate connections as building blocks.

Also shown in FIG. 4*b* are input pads that connect C-switches A' and B' and to the inputs I1 and I3 respectively as shown. In addition, also shown are output pads that connect the C-switches D', F' and E' to the outputs O1, O2, O3 and O4 respectively as shown. These input and output pads will be connected to the appropriate pins on the interface layer 110 by vias or glass feedthroughs in the protection wafer 108.

The switch matrix 102*a* also comprises DC bias ports 114 which are connected to DC tracks (represented by thin black lines). The DC tracks provide control lines to each SPDT RF MEMS structure for controlling the actuation of these structures. The DC tracks could provide step type control signals or pulse type control signals, depending on the actual type of SPDT RF MEMS switch used, to actuate the MEMS switches. The DC tracks may also be provided to the shunt air bridges, as shown in more detail in FIG. 4*c,* to optionally actuate these structures as is described below.

A corresponding lower portion 102*b* (not shown) of the bi-planar switch matrix 102 is laid out on the lower surface of the substrate 102 (hereafter referred to as switch matrix 102*b*). The switch matrix 102*b* will have an identical structure to that of switch matrix 102*a* except that the SPDT MEMS switches will have a configuration that mirrors the configuration of the SPDT switches in the switch matrix 102*a*. The mirror configuration involves rotating the plane, which contains the SPDT MEMS switches by 180° (this mirror configuration is clearly shown in FIG. 2*a*). In addition, each output of the upper half of the C-switch cells A', B', C', D', E' and F' will be connected to the lower half of the C-switch cells A', B', C', D', E' and F' in switch matrix 102*b* through vias.

Figure 4C:
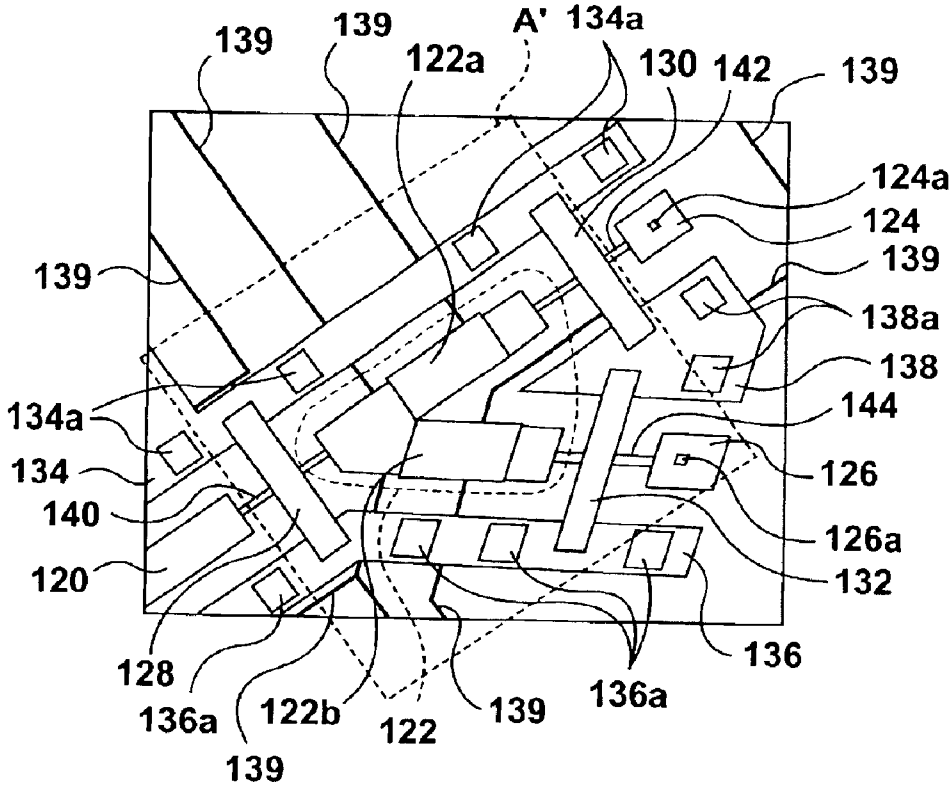
FIG. 4*c* is a top view of the upper level of one of the bi-planar switches used to construct the bi-planar switch matrix of FIG. 4*b;*

Referring now to FIG. 4*c,* the structure of the upper half of each of the bi-planar C-switches will be discussed using the bi-planar C-switches A' as an example. As it can be seen, the bi-planar C-switch A' comprises an input pad or input signal line 120, a SPDT MEMS switch 122 and two output pads 124 and 126 having vias 124*a* and 126*a.* The bi-planar C-switch A' also comprises three air-shunt bridges 128,130 and 132 (which are optional) and ground lines 134, 136 and 138 each having a plurality of ground vias 134*a,* 136*a* and 138*a* respectively. The bi-planar C-switch A' also has a number of DC control lines 139 that are connected to the SPDT MEMS switch 122, and to the air-shunt bridges 130 and 132.

An input signal provided to input pad 120 would propagate along transmission line 140 to the SPDT MEMS switch 122, which has two switch structures 122*a* and 122*b*. The DC control lines 139 actuates one of the switch structures 122*a* and 122*b* to be closed and the other to be open. If switch structure 122*a* is closed, the input signal is provided to transmission line 142, which is connected to output pad 124. Otherwise if switch 122*b* is closed, the input signal is provided to transmission line 144, which is connected to output pad 126.

The air shunt bridge 128 bridges the transmission line 140 and is connected to the ground lines 134 and 136. The air shunt bridge 128 is also separated from the transmission line 140 by an air gap (not shown). The air shunt bridge 128 removes unwanted CPW modes.

The air shunt bridges 130 and 132 are switch bridges that ground the transmission lines 142 and 144 respectively as shown in FIG. 4*c*. Since the air shunt bridges 130 and 132 function similarly, only the operation of air shunt bridge 130 will be described. The air shunt bridge 130 is separated from the transmission line 142 by an air gap (not shown) when a signal is being transmitted by the transmission line 142. However, when a signal is not being transmitted along the transmission line 142, the air shunt bridge 130 is actuated to contact the transmission line 142. Hence, the air shunt bridge 130 is connected to the DC control line 139 to receive control actuation signals. The air shunt bridge 130 connects the transmission line 142 to ground when a signal is not being transmitted to insure that any leakage signals that are transmitted along the transmission line 142 are not provided to the output pad 124. This improves the RF performance of the bi-planar C-switch A' by improving the RF isolation of the switch 122*a* when the switch 122*a* is open and a signal is not to be transmitted along the transmission line 142. As mentioned previously, the air shunt bridges 128, 130 and 132 are optional.

Figure 5:
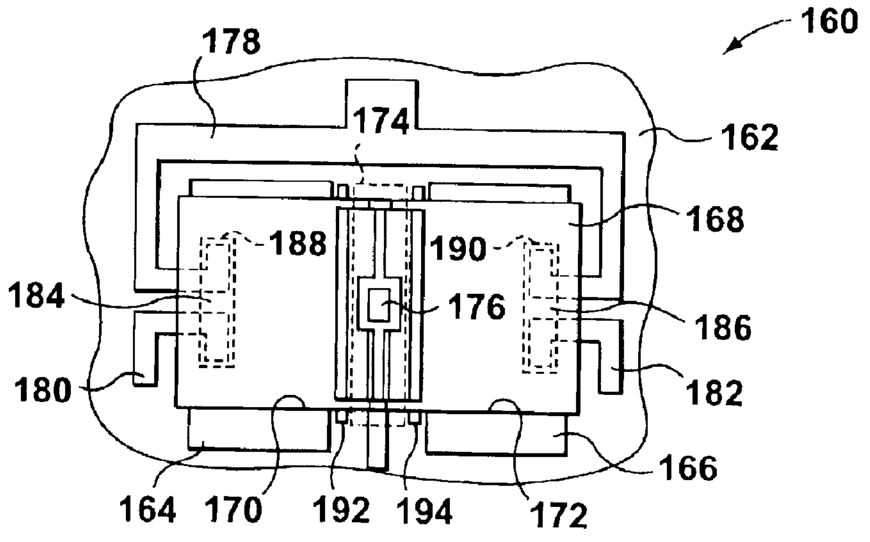
FIG. 5 (Prior Art)
FIG. 5 is a top view of a prior art single pole double throw MEMS switch which may be used in the switch matrix of FIG. 4.

To implement the MEMS SPDT switch 122, any SPDT RF MEMS switch known to those skilled in the art may be used. For instance, referring to FIG. 5, shown therein is a top view of a prior art RF SPDT MEMS switch 160 developed by Motorola Inc. and disclosed in U.S. Pat. No. 6,307,169. The RF SPDT MEMS switch 160 is fabricated on a suitable substrate 162, such as a silicon or gallium-arsenide, and comprises two electrically insulated control electrodes 164 and 166. The SPDT MEMS switch 160 also has a control electrode 168 comprised of a first cantilever section 170 and a second cantilever section 172. The control electrode 168 is electrically insulated from the control electrodes 164 and 166. A center hinge 174 is connected to both cantilever sections 170 and 172 and to an anchor structure 176 that is connected to the substrate 162. The SPDT MEMS switch 160 also has an input signal line 178 and two output signal lines 180 and 182, which are separated from the input signal line 178 by gaps 184 and 186 respectively. A contact 188, which may be a metal strip, is on the first cantilever section 170 for providing an electrical path between the input signal line 178 and the output signal line 180 when the first cantilever section 170 moves downwards due to control electrode 164. A second contact 190 is on the second cantilever section 172 for providing an electrical path between the input signal line 178 and the output signal line 182 when the second cantilever section 172 moves downwards due to control electrode 166. Travel stops 192 and 194 may be used to mechanically limit the movement of cantilever sections 170 and 172 respectively. Electrode 168 is connected to ground and command voltages are applied either to electrode 164 or electrode 166 to actuate the SPDT MEMS switch 160.

Figure 6A:
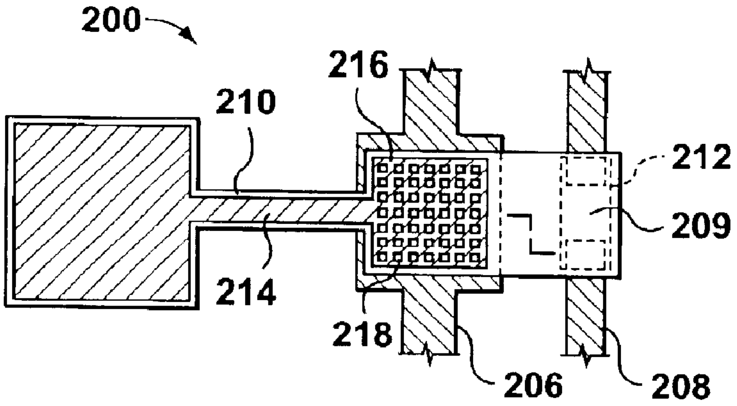
FIG. 6a (Prior Art)
FIG. 6*a* is a top view of a prior art single pole single throw MEMS switch which may be used in the switch matrix of FIG. 4.
Figure 6B:
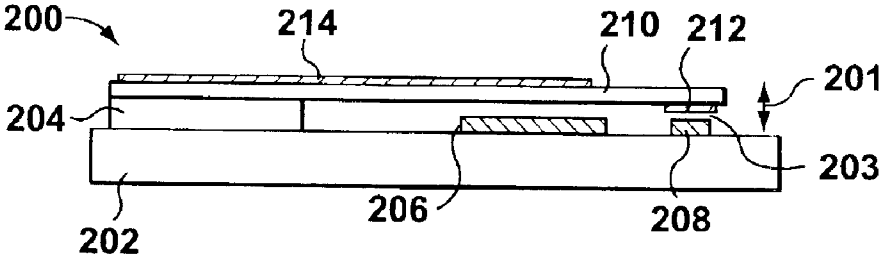
FIG. 6b (Prior Art)
FIG. 6*b* is a side view of the prior art single pole double throw MEMS switch of FIG. 6*a;*

Alternatively, to implement the MEMS SPDT switch 122, any two SPST RF MEMS switches known to those skilled in the art may be used. For instance, referring now to FIGS. 6*a* and 6*b*, shown therein is a prior art SPST MEMS switch 200 developed by Rockwell International Corporation and disclosed in U.S. Pat. No. 5,578,976. FIG. 6*a* shows a top view of the SPST MEMS switch 200 while FIG. 6*b* shows a side view of the SPST MEMS switch 200. The SPST MEMS switch 200 is fabricated on a substrate 202, which may be a semi-insulating gallium-arsenide substrate or any other suitable substrate, using generally known microfabrication techniques such as: masking, etching, deposition and lift-off as is commonly known to those skilled in the art. The SPST MEMS switch 200 is attached to the substrate 202 by an anchor structure 204, which may be formed as a mesa on the substrate 202 either by deposition buildup or by etching the surrounding material. A bottom electrode 206, typically connected to ground, and a signal line 208 are also created on the substrate 202. The electrode 206 and the signal line 208 comprise microstrips of a metal such as gold deposited on the substrate 202. The signal line 208 includes a gap 209 that is bridged by the actuation of the SPST MEMS switch 200 as indicated by the arrow 201. Attached to the anchor structure 204 is a cantilever arm 210 that is made from an insulating or semi-insulating material. The cantilever arm 210 comprises a metal strip 212 on a bottom side thereof overlying the signal line 208 and the gap 209 but separated from the signal line 208 by an air gap 203. The cantilever arm further comprises a top electrode 214 and a capacitor structure 216 on an upper side thereof. The capacitor structure 216 may optionally have a number of holes 218 therein for reducing weight.

In operation, the SPST MEMS switch 200 is normally in the "off" position due to the gap 209 in the signal line 208 and to the separation 203 between the contact 212 and the signal line 208. The SPST MEMS switch 200 is actuated to the "on" position by applying a voltage to the top electrode 214. When this happens electrostatic forces attract the capacitor structure 216 towards the bottom electrode 206. Actuation of the cantilever arm 210 under these electrostatic forces causes the contact 212 to touch the signal line 208, as indicated by the arrow 201, bridging the gap 209 and placing the signal line in the "on" state.

In FIGS. 4*a* to 4*c*, the switch matrix 102 was described as comprising the upper switch matrix 102*a* on the upper side of the substrate 104 and the lower switch matrix 102*b* on the lower side of the substrate 104. Alternatively, the upper switch matrix 102*a* and the lower switch matrix 102*b* could be implemented on different wafers 230 and 232 as shown schematically in FIG. 7. In this case the upper switch matrix 102*a* could be laid out on surface 230*a* of the wafer 230. To improve isolation the wafer 230 may have the surface opposite to surface 230*a* act as a ground plane. The lower switch matrix 102*b* could be laid out on surface 232*a* of wafer 232 and have the opposite face of the wafer 232 also act as a ground plane. The upper and lower switch matrices 102*a* and 102*b* face away from one another and have the signal lines connected together by vias, that pass through the ground planes; the vias are schematically represented as 238, 240, 242. The ground planes of the wafers 230 and 232 can be connected together through grounding vias 234 associated with switch matrix 102*a* and grounding vias 236 associated with switch matrix 102*b* to form a common ground plane. This structure enhances the isolation between the signal paths in the two planes and is easier to manufacture.

Referring now to FIGS. 8*a*–8*d*, shown therein is an isometric view of a representation of a 4×4 bi-planar electromechanical switch matrix 250 implemented using standard RF electromechanical SPST switches. The bi-planar electromechanical switch matrix 250 comprises an upper switch matrix 250*a* on an upper plane and a lower switch matrix 250*b* on a lower plane. The upper switch matrix 250*a* comprises input connectors for inputs I1 and I3 as well as output connectors for outputs O1, O2, O3 and O4. The lower switch matrix 250*b* comprises input connectors for inputs I2 and I4. The particular connectors used (i.e. SMA, TNC, etc.) would depend on the amount of power that is handled by the bi-planar electromechanical switch matrix 250.

In general, an RF electromechanical switch comprises three modules: a control module, an actuation module and an RF module. The RF module comprises an RF head which houses a plurality of reeds and RF connectors and an RF cover which comprises a cavity that provides a channel (corresponding to the position of the reeds) for implementing a transmission line for each signal path through which the RF signals are transmitted. The control module provides control signals, which may be short pulses, to the actuation module to move at least one of the reeds into a conducting state and at least one of the reeds into a non-conducting state. In the conducting position, a reed connects two of the RF connectors to transmit a signal there between while in the non-conducting state, a reed is grounded and does not connect two of the RF connectors so that a signal is not transmitted there between.

In the representation of the electromechanical bi-planar switch matrix 250, the control module is not shown although any suitable control module known to those skilled in the art may be used. Furthermore, the actuators of the actuation module are represented in block form by pairs of cylinders 252 (only one of which has been labeled for simplicity). Each of the actuators 252 may be a solenoid or any other suitable actuator known to those skilled in the art.

Figure 8A:
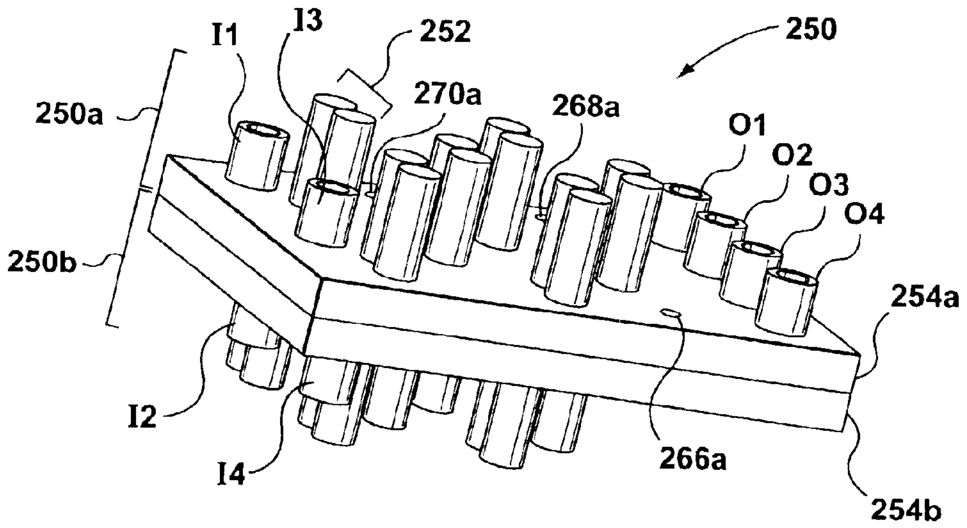
FIG. 8*a* is an isometric view of a bi-planar electromechanical switch matrix in accordance with the present invention.
Figure 8B:
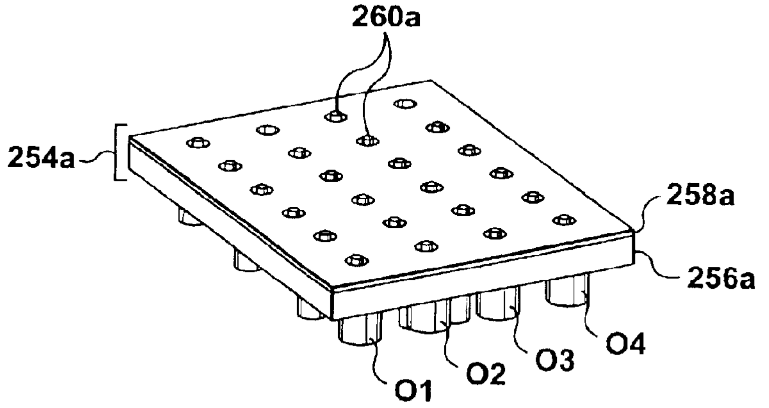
FIG. 8*b* is an isometric view of one of the RF modules of the bi-planar electromechanical switch matrix of FIG. 8*a;*

Referring now to FIG. 8*b*, shown therein is a bottom isometric view of the RF module 254*a* of the upper switch matrix 250*a*. The RF module 254*a* comprises an RF head 256*a* and an RF cover 258*a*. As can be seen, a number of vias 260*a* (only one of which is labeled for simplicity) protrude through the RF cover 258*a*. The lower switch matrix 250*b* also has an RF module 254*b*, which has components similar to that of RF module 254*a*. The RF module 254*b* is mounted adjacent to the RF module 254*a*, as shown in FIG. 8*a*, such that the vias 260*a* protrude into the RF head 254*b* and vias 260*b* protrude into RF head 254*a*.

Figure 8C:
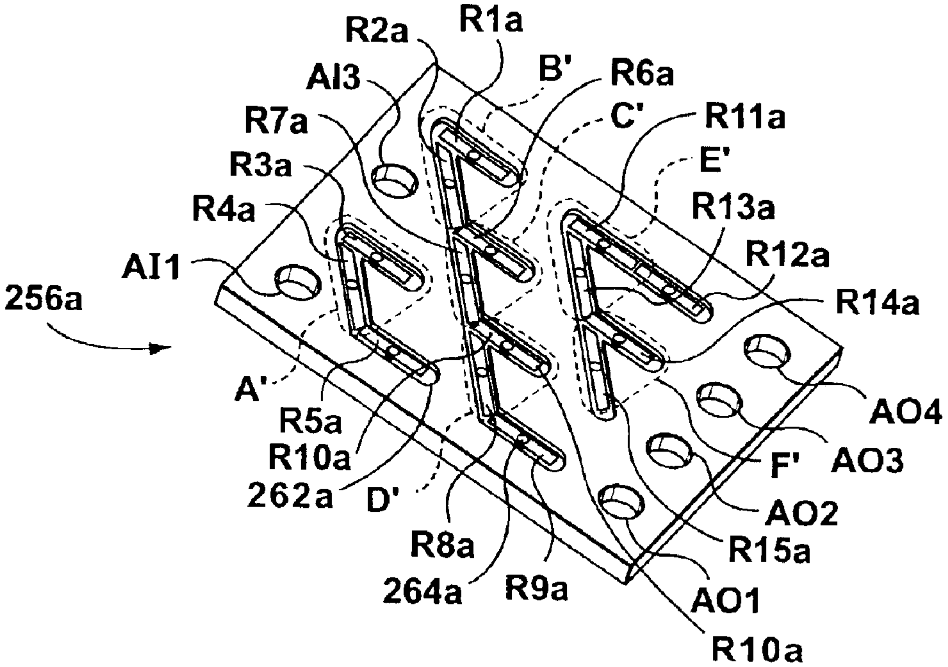
FIG. 8*c* is an isometric view of the RF head of the upper portion of the bi-planar electromechanical switch matrix of FIG. 8*a;*
Figure 8D:
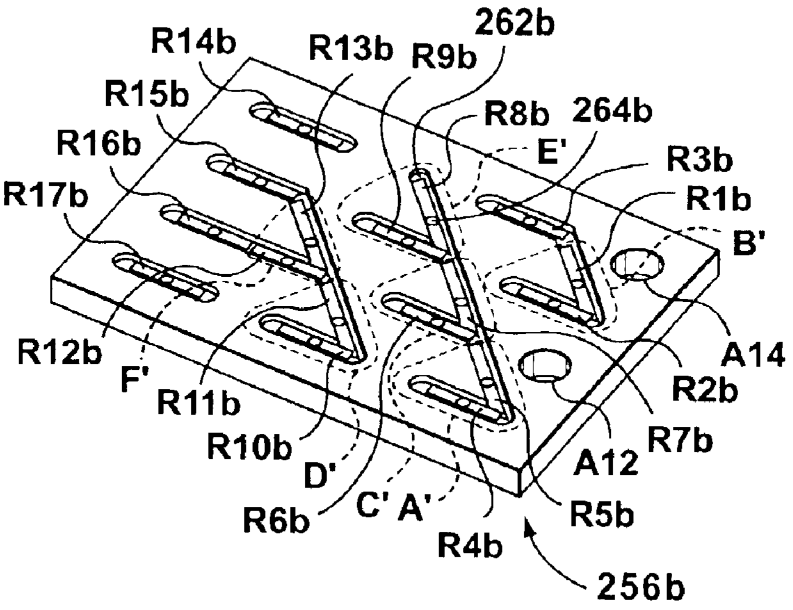
FIG. 8*d* is an isometric view of the RF head of the lower portion of the bi-planar electromechanical switch matrix of FIG. 8*a;*

Referring now to FIGS. 8*c* and 8*d*, shown therein is a bottom isometric view of RF head 256*a* of switch matrix 250*a* and a top isometric view of RF head 256*b* of switch matrix 250*b* respectively. The RF head 256*a* has apertures labeled AI1 and AI3 for receiving the input connectors corresponding to inputs I1 and I3, and apertures labeled AO1, AO2, AO3 and AO4 for receiving the output connectors corresponding to outputs O1, O2, O3 and O4. The RF head 256*a* also has a number of waveguide channels 262*a* (only one of which is labeled for simplicity) for receiving reeds R1*a*, R2*a*, . . . , R14*a*. The RF head 256*b* has apertures labeled AI4 and AI2 for receiving the input connectors corresponding to inputs I4 and I2 respectively. The RF head 256*b* also has a number of waveguide channels 262*b* (only one of which has been labeled for simplicity) for receiving reeds R1*b*, . . . , R17*b*. Each of the reeds Ria, Rib has a dielectric pin 264*a*, 264*b* (again only one of which is labeled for simplicity) that ensures that each reed Ria, Rib moves vertically. In addition, the reeds Ria do not overlap with one another and the reeds Rib do not overlap with one another.

The layout of the reeds in the RF head 256*b* corresponds to the signal paths on the upper plane of switch matrix 40 (see FIG. 3A). In particular, reeds R4*b* and R5*b*, reeds R1*b* and R2*b*, reeds R6*b* and R7*b*, reeds R10*b* and R11*b*, reeds R8*b* and R9*b* and reeds R12*b* and R13*b* correspond to the upper plane signal paths for bi-planar C-switches A', B', C', D', E' and F' respectively. Accordingly, these reeds are actuated such that only one reed of each of the pairs of reeds R4*b* and R5*b*, R1*b* and R2*b*, R6*b* and R7*b*, R8*b* and R9*b*, R10*b* and R11*b* and R12*b* and R13*b* is in the conducting state. Likewise, the majority of the reeds in RF head 256*a* correspond to the signal paths on the lower plane of switch matrix 40. In particular, reeds R3*a* and R4*a*, reeds R1*a* and R2*a*, reeds R6*a* and R7*a*, reeds R8*a* and R10*a*, reeds R11*a* and R13*a* and reeds R14*a* and R15*a* correspond to the upper plane signal paths for bi-planar C-switches A', B', C', D', E' and F' respectively. Accordingly, these reeds are actuated such that only one reed from each of the pairs of reeds R3*a* and R4*a*, R1*a* and R2*a*, R6*a* and R7*a*, R8*a* and R10*a*, R11*a* and R13*a* and R14*a* and R15*a* is in the conducting state.

Furthermore, reed R5*a* implements signal path 42 and reed R3*b* implements signal path 62 from FIG. 3*a*. Also, reeds R12*a* and R14*b* cooperate to implement signal path 64, reed R15*b* implements signal path 60, reed R16*b* implements signal path 52 and reeds R9*a* and R17*b* cooperate to implement signal path 44. Accordingly, reeds R5*a*, R9*a* and R12*a* are fixed reeds that are always held in the conducting state by permanent magnets 266*a*, 268*a* and 270*a* which are represented by circles in FIG. 10*a*. Likewise, reeds R3*b*, R14*b*, R15*b*, R16*b* and R17*b* are fixed reeds that are always held in the conducting state by permanent magnets (not shown). In addition, connections 46, 48, 50, 54, 56 and 58 from switch matrix 40 are not needed in electromechanical switch matrix 250 due to the use of vias to implement the ports that are connected by these connections. For instance, port P4 from bi-planar C-switch A' and port P1 from bi-planar C-switch C' can be implemented by one via and hence there is no need for connection 46.

Figure 9A:
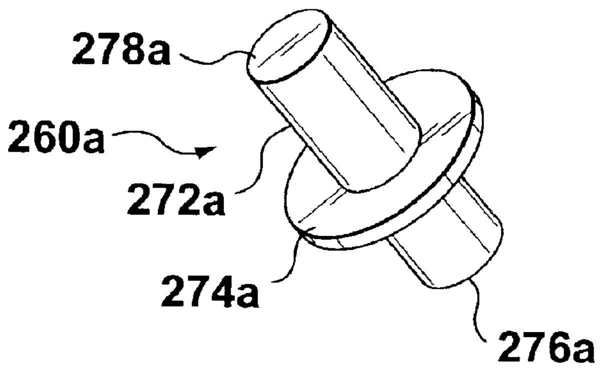
FIG. 9*a* is an isometric view of a via used in the bi-planar electromechanical switch matrix of FIG. 8.

Referring now to FIG. 9*a*, shown therein is an isometric view of one of the vias 260*a*. The via 260*a* comprises a conductive rod 272*a* that is inserted through a thin dielectric disc 274*a*. The rod 272*a* may be made from beryllium-copper and plated with gold to increase electrical conductivity. Alternatively, other suitable materials may be used. The dielectric disc 274*a* is made sufficiently thin so as to introduce only a small perturbation in the signal path or transmission line that via 260*a* is connected to. The small perturbation may be reduced by using various impedance matching techniques, as is commonly known to those skilled in the art, such as varying the geometry of the waveguide channels 262*a* in the vicinity of the via 260*a*.

Figure 9B:
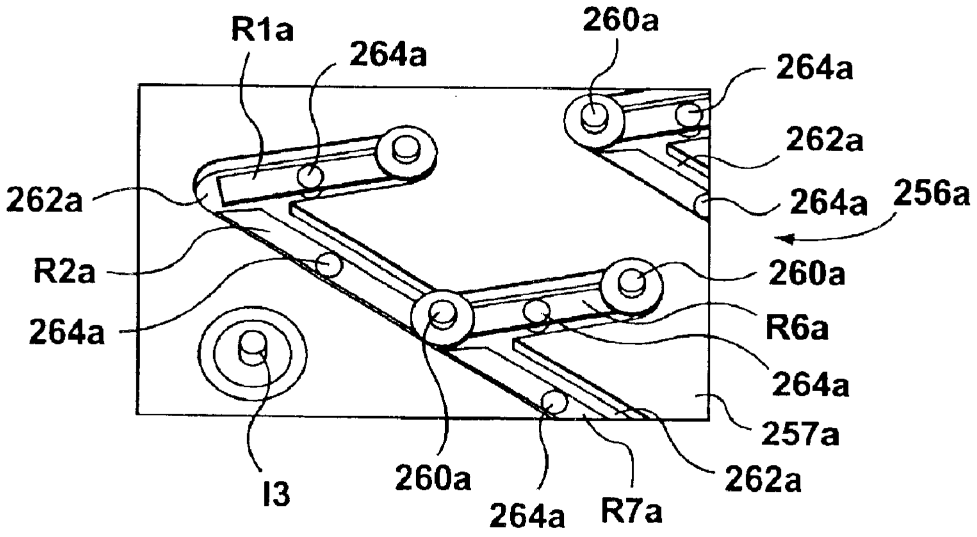
FIG. 9*b* is a top view of a portion of the RF head of FIG. 8*c;*

Referring now to FIG. 9*b*, shown therein is a portion of the RF head 256*a* of FIG. 8*c*. Each via 260*a* is inserted in a grounding plate (not shown) such that the dielectric disc 274*a* sits on top of the RF head 256*a*. The surface 257*a* of the RF head 256*a* as well as the sides of each waveguide channel 262*a* acts as a ground plane. Accordingly, a reed makes contact with the bottom of a waveguide channel that it is contained within when the reed is not in a conducting state. Alternatively, a reed makes contact with the conducting rod 272*a* of via 260*a* when the reed is in a conducting state. Accordingly, the rod 272*a* of via 260*a* does not make contact with any surfaces of the RF head 256*a*. Hence the use of the dielectric disc 274*a*, which insulates the rod 272*a* from the surfaces of the RF head 256*a*.

Figure 10:
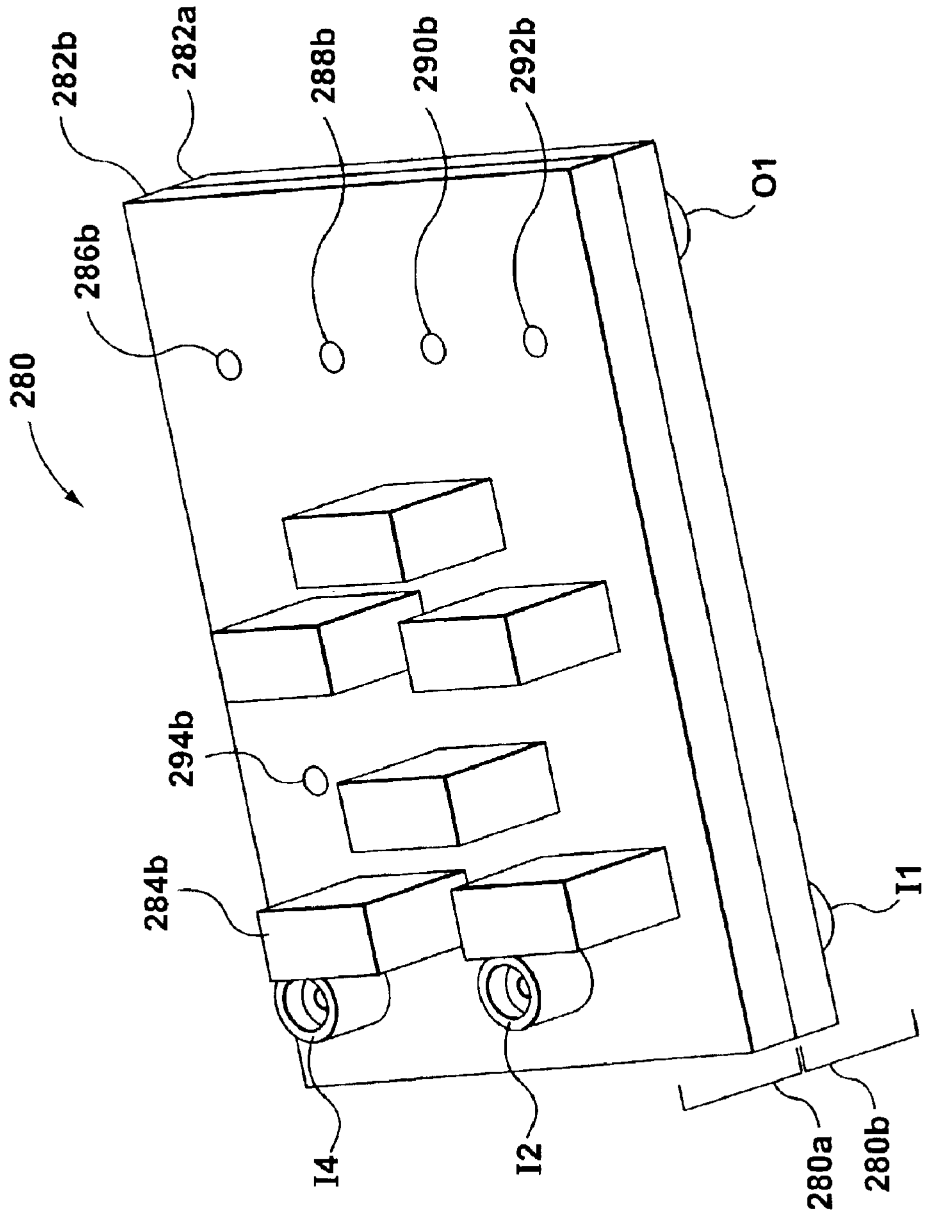
FIG. 10 is a bottom isometric view of an alternative embodiment of a bi-planar electromechanical switch matrix.

Referring now to FIG. 10, shown therein is a bottom isometric view of an alternative embodiment of a bi-planar electromechanical switch 280, which utilizes SPDT switches. The bi-planar switch 280 has the same connectors for the inputs I1, . . . , I4 and outputs O1, . . . , O4 in the same position as was the case for the bi-planar switch 250. The bi-planar switch 280 also comprises RF modules 282*a* and 282*b* for upper and lower switch matrices 280*a* and 280*b*. The control module for the switch 280 is not shown and the actuation modules 284*b* of the lower switch matrix 280*b* are shown as rectangular blocks (only one of which is labeled for simplicity). The upper switch matrix 280*a* also has such actuation modules but they are not shown in FIG. 10. Each actuation module 284*b* may be implemented using any suitable actuation module for an SPDT electromechanical switch that is known to those skilled in the art. The RF module 282*b* also comprises permanent magnets 286*b*, 288*b*, 290*b*, 292*b* and 294*b* for holding some reeds fixed in position as explained previously for the bi-planar switch 250.

The reeds, waveguide channels and vias of the switch 280 are similar to those shown for switch 250. However, since the bi-planar switch 280 utilizes SPDT switches, each of the following pairs of reeds from the bi-planar switch 250 could be implemented as SPDT structures in switch 280: reeds R4*b* and R5*b*, reeds R1*b* and R2*b*, reeds R6*b* and R7*b*, reeds R10*b* and R11*b*, reeds R8*b* and R9*b*, reeds R12*b* and R13*b*, reeds R3*a* and R4*a*, reeds R1*a* and R2*a*, reeds R6*a* and R7*a*, reeds R8*a* and R10*a*, reeds R11*a* and R13*a* and reeds R14*a* and R15*a*. Vias would also be used as explained previously for the bi-planar switch 250 to transmit signals from the upper switch matrix 280*a* to the lower switch matrix 280*b*.

Figure 11:
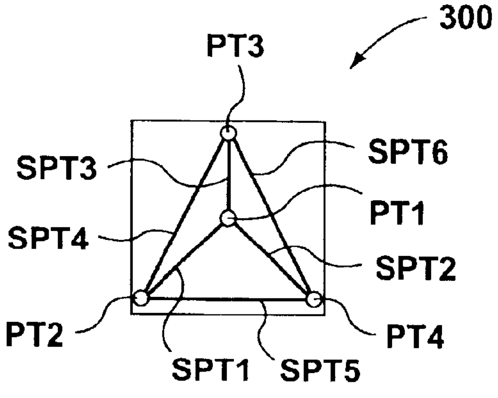
FIG. 11 (Prior Art)
FIG. 11 is a top view of a schematic of a prior art T-switch.

The bi-planar switch configuration may be applied to other types of RF switches such as T-switches and R-switches (an R-switch is very similar to a T-switch and has the same number of ports as a T-switch but one less signal path). Referring now to FIG. 11, shown therein is a schematic of a common embodiment of a prior art T-switch 300 which may be implemented as an RF electromechanical switch or an RF MEMS switch as is known to those skilled in the art. The T-switch 300 is implemented on a single plane and comprises four ports PT1, PT2, PT3 and PT4 and six signal paths or transmission lines SPT1, SPT2, SPT3, SPT4, SPT5 and SPT6. Signal path SPT1 connects port PT1 to port PT2, signal path SPT2 connects port PT1 to port PT4 and signal path SPT3 connects port PT1 to port PT3. Signal path SPT4 connects port PT2 to port PT3, signal path SPT5 connects port PT2 to port PT4 and signal path SPT6 connects port PT3 to port PT4.

The signal paths SPT1, SPT2, SPT3, SPT4, SPT5 and SPT6 can be implemented with single-pole single-throw (SPST) switches in which a signal path may be closed (i.e. non-conducting) or open (i.e. conducting). In use, the T-switch 300 has three positions. In the first position, port PT1 is connected to port PT3 and port PT2 is connected to port PT4. In the second position, port PT1 is connected to port PT2 and port PT3 is connected to port PT4. In the third position, port PT1 is connected to port PT4 and port PT2 is connected to port PT3.

Figure 12A:
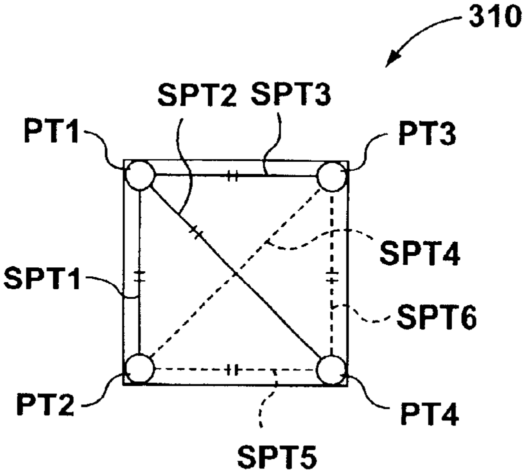
FIG. 12*a* is a top view of a schematic of a bi-planar T-switch in accordance with the present invention.
Figure 12B:
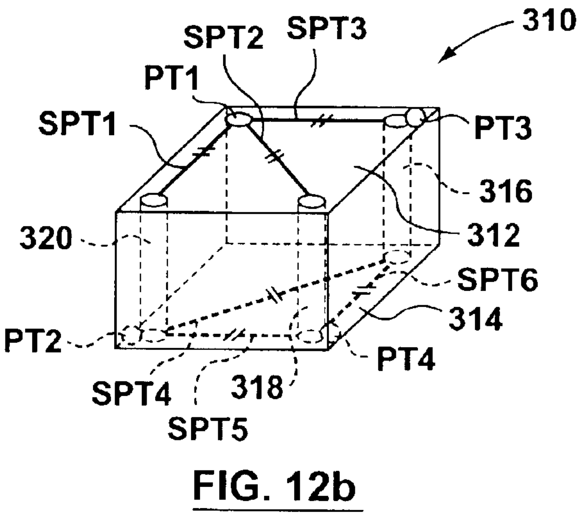
FIG. 12*b* is an isometric view of the schematic of the bi-planar T-switch of FIG. 12*a;*

Referring now to FIGS. 12*a* and 12*b*, shown therein is a schematic of a bi-planar T-switch 310 in accordance with present invention in which at least one of the signal paths have been placed on different planes. FIG. 12*a* depicts a top-view of the bi-planar T-switch 310 and FIG. 12*b* depicts an isometric view of the bi-planar T-switch 310. As shown in FIG. 12*a*, the bi-planar T-switch 310 has ports PT1 and PT2 on a first side of the bi-planar switch 310 and ports PT3 and PT4 on a second side of the bi-planar switch 310. Ports PT2 and PT4 are in the same position as for switch 300. As is more easily seen in FIG. 12*b*, the bi-planar T-switch 310 has an upper plane or surface 312 in which the ports PT1 and PT3 and the signal paths SPT1, SPT2 and SPT3 are located and a lower plane or surface 314 in which the ports PT2 and PT4 and the signal paths SPT4, SPT5 and SPT6 are located. The planes 312 and 314 could be two RF modules connected by vias if the bi-planar switch 310 was implemented using electromechanical switches as discussed previously for the bi-planar switch 30. Alternatively, the planes 312 and 314 could be two sides of an IC substrate or the surfaces of two IC substrates or wafers if the bi-planar switch 310 was implemented using RF MEMS switches. The bi-planar T-switch 310 also has signal vias 316, 318 and 320, which are used to connect a signal path located on one of the planes 312 and 314 to an output port located on the other of the planes 312 and 314. The ports PT1, PT2, PT3 and PT4 can be connected to an external interface using conventional methods as is commonly known by those skilled in the art.

The bi-planar T-switch 310 may be constructed as either an electromechanical switch or an RF MEMS switch as explained previously for the bi-planar C-switch 30. In both cases, each of the signal paths SPT1, . . . , SPT6 can be implemented by any suitable SPST switch as is known to those skilled in the art. Alternatively, two out of the three signal paths SPT1, SPT2 and SP3 may be implemented by a SPDT switch and the remaining signal path implemented by a SPST switch. Likewise, signal paths SPT4 and SPT5 or SPT4 and SPT6 or SPT5 and SPT6 may be implemented using a SPDT switch with the remaining path being implemented with a SPST switch. Alternatively, all three signal paths SPT1, SPT2 and SPT3 may be implemented by a single-pole triple throw switch (SP3T).

Figure 13A:
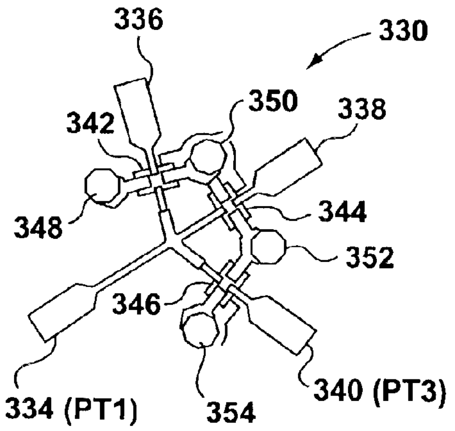
FIG. 13a (Prior Art)
FIG. 13*a* is a top view of a prior art single pole triple throw RF MEMS switch that can be used to implement the upper plane of the bi-planar T-switch of FIG. 12.
Figure 13B:
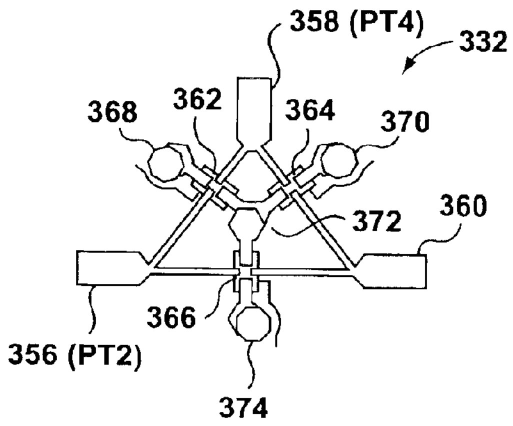
FIG. 13b (Prior Art)
FIG. 13*b* is a top view of a prior art delta RF MEMS switch that can be used to implement the lower plane of the bi-planar T-switch of FIG. 12.

Referring now to FIGS. 13*a* and 13*b*, shown therein are two RF MEMS switch structures, which can be used to implement an RF MEMS version of the bi-planar T switch 310. FIG. 13*a* depicts a top view of a prior art RF MEMS SP3T switch 330 which may be used to implement the structure on the top plane 312 of the bi-planar T switch 310. FIG. 13*b* depicts a bottom view of a prior art RF MEMS delta switch 332 which may be used to implement the structure on the bottom plane 314 of the bi-planar T switch 310. The RF MEMS SP3T switch 330 and the RF MEMS delta switch 332 may be connected by signal vias.

Referring now to FIG. 13*a*, the SP3T switch 330 comprises four pads 334, 336, 338 and 340. Pads 334 and 340 are connected to a port similar to ports PT1 and PT3 of the bi-planar switch 310 (connection not shown) while pads 336 and 338 are each connected to a via to connect with ports similar to ports PT2 and PT4 respectively of the bi-planar switch 310. The SP3T switch 330 also has three series RF MEMS SPST switches 342, 344 and 346 that implement the signal paths SPT1, SPT2 and SPT3 respectively. Situated beside RF MEMS switch 342 are DC vias 348 and 350 which provide DC control signals to actuate the RF MEMS switch 342. Likewise on either side of RF MEMS switch 344 are DC vias 350 and 352 and on either side of RF MEMS switch 346 are DC vias 352 and 354, which similarly provide DC control signals for actuation of the switches 344 and 346.

Referring now to FIG. 13*b*, the RF MEMS delta switch 332 comprises three pads 356, 358 and 360 which are connected to (connections not shown) to ports PT2 and PT3 and a via which is connected to port PT3 respectively of the bi-planar switch 310. The pads 356, 358 and 360 are connected to pads 336, 338 and 340 respectively of the SP3T switch 330 through vias or other suitable means. The RF MEMS delta switch 332 also comprises three SPST MEMS switches 362, 364 and 366 in a delta configuration to implement the switching functionality of the signal paths SPT5, SPT6 and SPT4 respectively. Each of the SPST MEMS switches also have pads on either side of the SPST switches to receive DC control signals to actuate the switches. SPST MEMS switch 362 has dc pads 368 and 372 on either side thereof, SPST MEMS switch 364 has dc pads 370 and 372 on either side thereof and SPST MEMS switch 366 has dc pads 372 and 376 on either side thereof. Each of the dc pads contact the appropriate pins on an interface layer (such as layer 110 shown in FIG. 4*a*) through vias or other suitable means.

Figure 7:
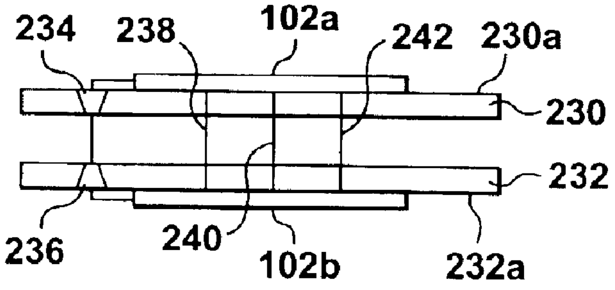
FIG. 7 is a side view of two wafers which can provide two planes for the bi-planar switch matrix of FIG. 4.

The RF MEMS SP3T switch 330 may be implemented on the upper surface of a substrate (not shown) that sits on the top of an interface layer (similar to substrate 104 shown in FIG. 4*a*); hence the need for DC vias. Alternatively, instead of using DC vias proximal to the SP3T switch 330 as currently shown in FIG. 13*a*, DC bias ports and DC tracks may be used as shown previously in FIGS. 4*b* and 4*c*. In this case, the RF MEMS delta switch 332 may be implemented on the opposite surface of the substrate such that the delta switch 332 is directly opposite the SP3T switch 330. Alternatively, these two switches 330 and 332 may be on the surfaces of two separate wafers as shown in FIG. 7 with appropriate connections for RF signals, dc control signals and ground lines.

Figure 14A:
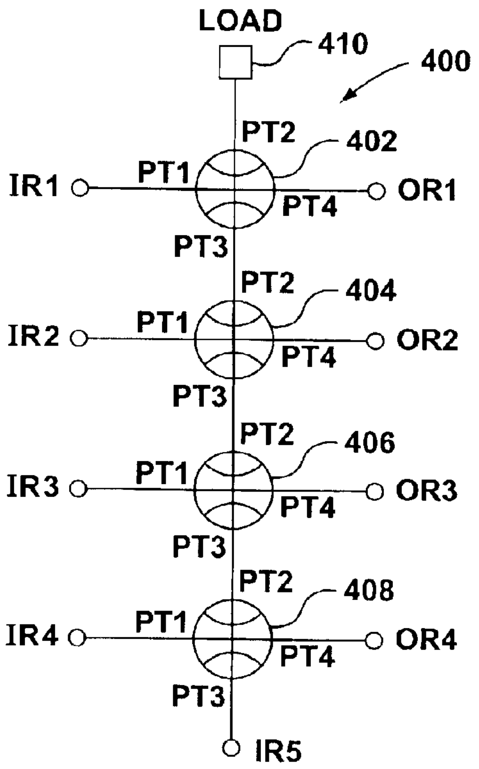
FIG. 14a (Prior Art)
FIG. 14*a* is a top view of a prior art 4 T-switch redundancy structure.

Referring now to FIG. 14*a*, shown therein is a prior art 4 T-switch output redundancy ring 400, which is the second type of typical structure used in spacecraft applications. The redundancy ring 400 comprises T-switches 402, 404, 406 and 408, four inputs IR1, IR2, IR3 and IR4, a spare input IR5, four outputs OR1, OR2, OR3 and OR4 and a load 410 connected as shown. The load 410 is used to avoid the reflection of the spare input IR5 when not connected to any of the outputs. The redundancy ring 400 comprises the plurality of T-switches 402, 404, 406 and 408 so that in the event that one of the input channels will fail (due to a TWTA failure), the spare input channel IR5 can be routed to the corresponding output so that all the output ports OR1, OR2, OR3 and OR4 are still active. Since the structure is reciprocal it can also be used as an input redundancy ring if one can consider the outputs as inputs and vice-versa. In this "reverse case", one of the "input" channels OR1, OR2, OR3 and OR4 is routed to a different "output" channel IR1, IR2, IR3, IR4 and the input IR5 still replaces one of the failed input channels.

Figure 14B:
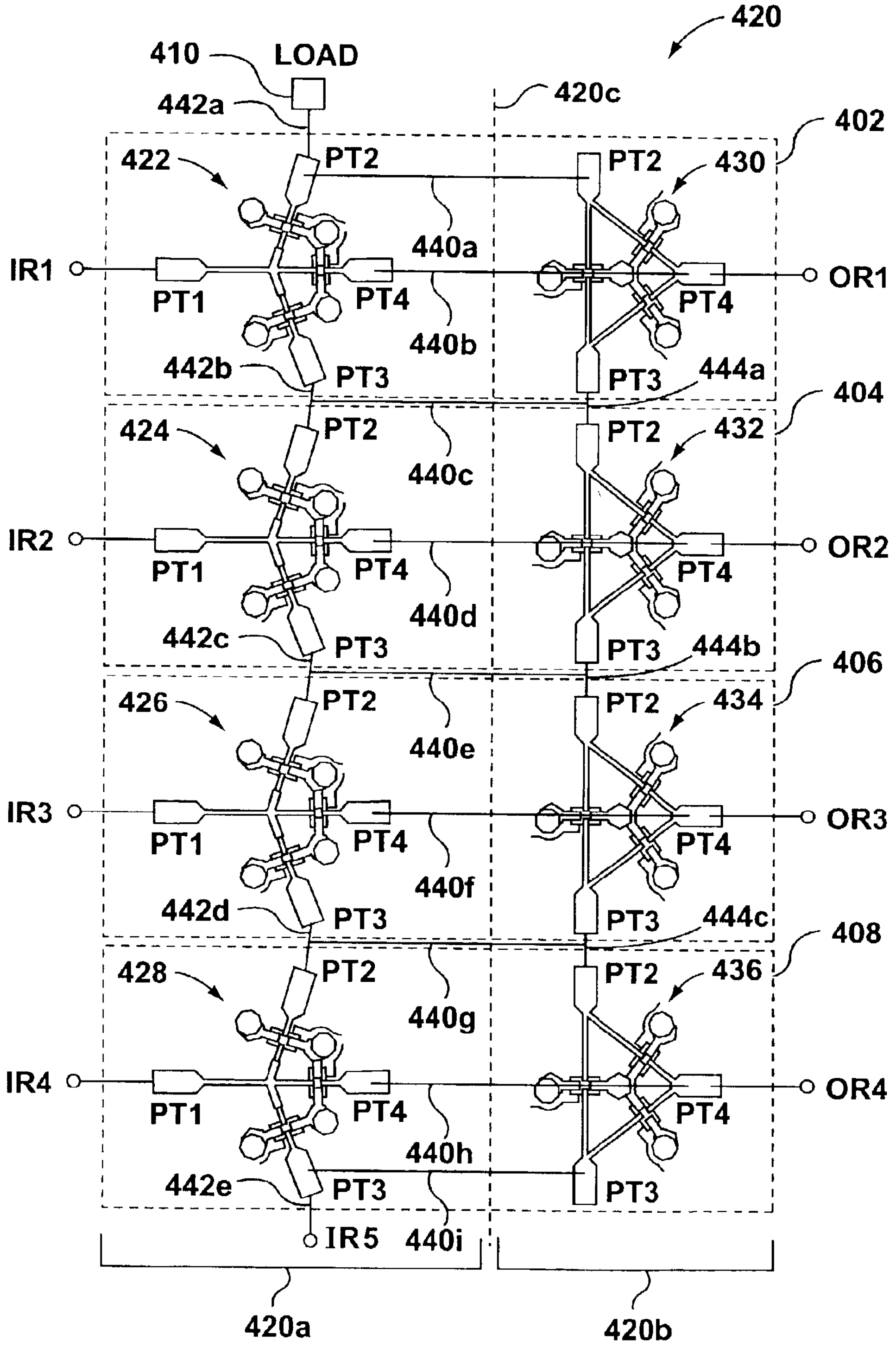
FIG. 14*b* is a top view of the upper and lower planes of a bi-planar 4 T-switch redundancy structure in accordance with the present invention.

Referring now to FIG. 14*b*, shown therein is an "unfolded" top view of the two planes of a bi-planar 4 T-switch redundancy ring 420, which is implemented using RF MEMS switches. The ring 420 comprises a first plane or surface 420*a* and a second plane or surface 420*b* (the two top views are separated by dotted line 420*c* which also represents the ground plane). On the first plane 420*a* there are a plurality of switches 422, 424, 426 and 428, which are in accordance with the SP3T switch 330 shown in FIG. 13*a*. On the second plane 420*b* there are a plurality of switches 430, 432, 434 and 436 which are in accordance with the delta switch 332 shown in FIG. 13*b*.

The SP3T switch 422 and the delta switch 430 implement the T-switch 402 and the appropriate pads from each of these switches are connected with vias 440*a*, 440*b* and 440*c*. The SP3T switch 424 and the delta switch 432 implement the T-switch 404 and the appropriate pads from each of the switches are connected with vias 440*c*, 440*d* and 440*e*. The SP3T switch 426 and the delta switch 434 implement the T-switch 406 and the appropriate pads from each of these switches are connected with vias 440*e*, 440*f* and 440*g*. The SP3T switch 428 and the delta switch 436 implement the T-switch 408 and the appropriate pads from each of these switches are connected with vias 440*g*, 440*h* and 440*i*. It can be seen that adjacent switches share vias 440*c*, 440*e*, 440*g* and 440*i*. Furthermore, SP3T switches 422, 424, 426 and 428 are interconnected with one another and with the load 410 and the spare input IR5 using connections 442*a*, 442*b*, 442*c*, 442*d* and 442*e*, which are conductive interconnect traces as is commonly known to those skilled in the art of IC technology. Likewise, the appropriate pads of the delta switches 430, 432, 434 and 436 are interconnected with one another using connections 444*a*, 444*b* and 444*c* which are also implemented with conductive interconnect traces.

It should be understood that various modifications may be made to the embodiments described and illustrated herein, without departing from the present invention, the scope of which is defined in the appended claims. For instance, bi-planar RF MEMS switch matrices and bi-planar electromechanical switch matrices can be constructed with any number of bi-planar switches and any number of inputs and outputs. In addition, the bi-planar T-switch can be implemented using electromechanical RF switches by following the embodiments shown in FIGS. 8–10 for the bi-planar C-switches. The bi-planar switch concept can also be extended to a SPDT switch in which one of signal paths is placed on one plane and the other signal path is placed on another plane. The ports for the SPDT switch may be placed on either plane and appropriate vias inserted for connecting a signal path with at least one of the ports. Furthermore, the concept of using multiple planes to build a switch or a switch matrix, as described herein may be extended to more than two planes.

It should also be understood that the various RF MEMS and electromechanical RF switch embodiments can be used to construct a single bi-planar C-switch cell. Furthermore, the 4×4 bi-planar switch matrices discussed herein were provided as examples only and are not meant to limit the invention. In addition, the term switch matrices and redundant T-switch network are understood to be examples of microwave switch networks.

What is claimed is:

1. A microwave switch for transmitting signals, the switch comprising:

a) a plurality of ports, at least one of the plurality of ports being located on a first plane and at least one of the plurality of ports being located on a second plane;

b) a plurality of signal paths for selective transmission of said signals, each signal path being disposed between a respective pair of said ports and each signal path having a conducting state in which signal transmission occurs between the respective pair of ports and a non-conducting state in which signal transmission does not occur between the respective pair of ports, at least one of the plurality of signal paths being located on the first plane and at least one of the signal paths being located on the second plane;

c) a plurality of actuators, each actuator being adapted to actuate at least one of the signal paths between the conducting and non-conducting states; and d) transmission means for connecting one of the plurality of ports on the first plane to one of the plurality of ports on the second plane.

whereby, in any of the planes, there are no cross over points between the signal paths.

2. The microwave switch of claim 1, wherein the transmission means comprises vias, wherein each via connects one of the ports on one of the planes to at least one of the signal paths on the other plane.

3. The microwave switch of claim 1, wherein half of the signal paths are on the first plane and half of the signal paths are on the second plane.

4. The microwave switch of claim 1, wherein the microwave switch is a micro-electromechanical switch with the first plane being a surface of a first substrate and the second plane being a surface of a second substrate.

5. The microwave switch of claim 1, wherein the microwave switch is a micro-electromechanical switch with the first plane being a first surface of a substrate and the second plane being another surface of the substrate.

6. The microwave switch of claim 1, wherein the microwave switch is one of a micro-electromechanical SPDT-switch, a micro-electromechanical C-switch, a micro-electromechanical T-switch and a micro-electromechanical R-switch.

7. The microwave switch of claim 1, wherein said first and second planes are parallel to and spaced apart from each other.

8. The microwave switch of claim 1, wherein said microwave switch is an electromechanical switch comprising:

a) a first RF module having a waveguide channel and a reed for each signal path on the first plane, and a connector for each port on the first plane; and, b) a second RF module having a waveguide channel and a reed for each signal path on the second plane, and a connector for each port on the second plane wherein the transmission means includes vias.

9. A microwave switch network comprising, a) a plurality of inputs;

b) a plurality of outputs;

c) a plurality of switches, with at least one of the switches being connected to the inputs and at least one of the switches being connected to the outputs;

wherein, the microwave switch network comprises two planes and at least some of the switches are bi-planar switches each having portions constructed on both of the planes for allowing the bi-planar switches to be connected to one another with no cross over points on any of the planes.

10. The microwave switch network of claim 9, wherein each bi-planar switch comprises:

a) a plurality of ports;

b) a plurality of signal paths for selective transmission of signals between the ports, each signal path being disposed between a respective pair of the ports and each signal path having a conducting state in which signal transmission occurs between the respective pair of ports and a non- conducting state in which signal transmission does not occur between the respective pair of ports; and, c) a plurality of actuators, each actuator being adapted to actuate at least one of the signal paths between the conducting and non-conducting states;

wherein, at least one of the ports and at least one of the signal paths are located on a first plane and another of the ports and another of the signal paths are located on a second plane, whereby, in any of the planes, there are no cross over points between the signal paths.

11. The microwave switch of claim 10, wherein each bi-planar switch further comprises vias, wherein each via connects one of the ports on one of the planes to at least one of the signal paths on the other plane.

12. The microwave switch of claim 10, wherein half of the signal paths are on the first plane and half of the signal paths are on the second plane.

13. The microwave switch network of claim 9, wherein each bi-planar switch is a micro-electromechanical switch and the first plane is a surface of a first substrate and the second plane is a surface of a second substrate.

14. The microwave switch network of claim 9, wherein each bi-planar switch is a micro-electromechanical switch and the first plane is a first surface of a substrate and the second plane is another surface of the substrate.

15. The microwave switch of claim 10, wherein each microwave switch is a bi-planar electromechanical switch, having a waveguide channel and a reed for each signal path.

16. The microwave switch of claim 15, wherein said portions of the plurality of bi-planar electromechanical switches on said first plane are housed in a first RF module and the portions of the plurality of bi-planar electromechanical switches on said second plane are housed in a second RF module, the signal paths on the first plane being connected to the signal paths on the second plane by a plurality of vias.

17. The microwave switch network of claim 9, wherein said first and second planes are parallel to and spaced apart from each other.

* * * * *